United States Patent
Young et al.

[11] Patent Number: 6,052,608
[45] Date of Patent: Apr. 18, 2000

[54] IMPLANTABLE MEDICAL ELECTRODE CONTACTS

[75] Inventors: Terrence R. Young, Taunton; Timothy A. Beardsley, Kingston, both of Mass.

[73] Assignee: Johnson & Johnson Professional, Inc., Raynham, Mass.

[21] Appl. No.: 09/050,460

[22] Filed: Mar. 30, 1998

[51] Int. Cl.$^7$ .................................................. A61B 5/04
[52] U.S. Cl. ................... 600/378; 600/393; 607/116; 29/825
[58] Field of Search ...................... 600/372, 373, 600/377, 378, 350–353; 607/115–118, 139, 140, 148, 149, 152; 29/825

[56] References Cited

U.S. PATENT DOCUMENTS

| | | | |
|---|---|---|---|
| 372,647 | 11/1887 | Williams | 607/149 |
| 3,612,061 | 10/1971 | Collins et al. | 607/148 |
| 4,734,963 | 4/1988 | Ishiyama | 29/25.35 |
| 4,735,208 | 4/1988 | Wyler et al. | 128/642 |
| 4,819,647 | 4/1989 | Byers et al. | 607/116 |
| 4,887,614 | 12/1989 | Shirakami et al. | 128/798 |
| 4,890,623 | 1/1990 | Cook et al. | 128/642 |
| 4,903,702 | 2/1990 | Putz | 600/377 |
| 4,969,468 | 11/1990 | Byers et al. | 128/642 |
| 4,971,070 | 11/1990 | Holleman | 128/784 |
| 5,201,903 | 4/1993 | Corbett, III et al. | 29/872 |
| 5,205,297 | 4/1993 | Montecalvo et al. | 128/798 |
| 5,235,977 | 8/1993 | Hirschberg et al. | 607/5 |
| 5,255,692 | 10/1993 | Neubauer et al. | 607/122 |
| 5,265,608 | 11/1993 | Lee et al. | 600/377 |
| 5,342,413 | 8/1994 | Hirschberg et al. | 607/126 |
| 5,375,594 | 12/1994 | Cueva | 128/642 |
| 5,617,865 | 4/1997 | Palczewska et al. | 128/662.03 |
| 5,643,338 | 7/1997 | Bornzin et al. | 607/123 |
| 5,645,580 | 7/1997 | Moaddeb et al. | 607/122 |

FOREIGN PATENT DOCUMENTS

| | | | |
|---|---|---|---|
| 396048 | 11/1990 | European Pat. Off. | 600/390 |
| 0 585 933 | 3/1994 | European Pat. Off. | G01N 27/30 |
| 2124704 | 11/1972 | Germany | 600/390 |
| 93/20887 | 10/1993 | WIPO | A61N 1/04 |
| WO9602298 | 7/1995 | WIPO | A61N 1/05 |

OTHER PUBLICATIONS

Anthony L. Owens, et al., "Multi–electrode array for measuring evoked potentials from surface of ferret primary auditory cortex", Elsevier Science B.V., Journal of Neuroscience Methods 58, 1995, 209–220.

Anderson, D.J. et al., "Batch–Fabricated Thin–Film electrodes for Stimulation of the Central Auditory System", IEEE Transactions on Biomedical Engineering, vol. 36, No. 7, Jul. 7, 1989, pp. 693–703.

Peckerar, M. et al., "Passive Microelectrode Arrays for Recording of Neural Signals: A Simplified Fabrication Process" Review of Scientific Instruments, vol. 62, No. 9, Sep. 1991, pp. 2276–2280.

*Primary Examiner*—Lee Cohen
*Attorney, Agent, or Firm*—Nutter, McClennen & Fish, LLP

[57] ABSTRACT

An implantable medical electrode supports at least one conductive contact having a rounded protrusion adapted for contacting a treatment site of a patient in use and an edge portion bordering at least a portion of the rounded protrusion. The electrode includes a first flexible insulating layer and a second flexible insulating layer having at least one aperture. In assembly, the conductive contact is positioned between the first and second insulating layers with the rounded protrusion of the contact aligned with, and extending into the aperture. In one embodiment, the rounded protrusion extends through the aperture to terminate at an apex beyond the second insulating layer.

17 Claims, 2 Drawing Sheets

IMPLANTABLE MEDICAL ELECTRODE CONTACTS

CROSS-REFERENCE TO RELATED APPLICATIONS

Not applicable.

STATEMENTS REGARDING FEDERALLY SPONSORED RESEARCH

Not applicable.

BACKGROUND OF THE INVENTION

Implantable medical electrodes are used in a variety of medical applications. One such application is the sensing of cortical electrical activity which can be analyzed to identify the foci of epileptogenic brain for removal. The same implantable medical electrodes which are used to sense cortical electrical activity passively can also be used to stimulate various regions of the brain to further analyze the foci of epileptogenic brain in order to enhance the safety and effectiveness of epileptogenic brain removal.

One conventional type of implantable medical electrode used for sensing cortical electrical activity is a depth electrode which is a relatively narrow, typically cylindrical structure with conductive ring electrodes spaced along its length. A depth electrode is an intracortical device that is inserted into the brain tissue. Depth electrodes provide electrical contact to, and thus information regarding electrical activity within the brain itself.

Another type of implantable medical electrode for use in sensing cortical electrical activity is referred to as a strip electrode. A strip electrode is inserted between the dura and the cortex and does not penetrate the brain. Strip electrodes typically include a flexible, substantially flat strip of dielectric material supporting one or more flat electrical contacts with which cortical electrical activity on the surface of the brain is stimulated and/or sensed. Each flat contact is connected to a proximal end of an insulated lead wire having a distal end suitable for coupling to electrical stimulation and/or monitoring apparatus. It is important that the strip electrode be flexible in order to conform to the patient's cortex.

More particularly, strip electrodes generally include two dielectric layers between which the flat electrical contacts are located. One of the dielectric layers has a plurality of apertures therethrough, with each aperture aligned with a corresponding contact so as to expose at least a portion of the contact.

It is critical that each of the flat contacts comes into contact with the cortex and, once in contact, remains in the same fixed position relative to the cortex. Knowledge of the exact positions of the strip electrode contacts relative to the cortex is necessary in order to properly interpret the electrical readings.

Conventionally, providing a strip electrode with a certain amount of thickness, such as on the order of 0.020–0.030 inches, has been felt to maintain adequate positioning of the electrode once implanted. This thickness has also been felt to enhance support of the lead wires by preventing them from breaking away from the contacts and/or becoming dislodged within the strip electrode. However, it is also desirable to make the strip electrode relatively thin in order to avoid raising intracranial pressure when the dura is closed, particularly in pediatric cases, in which there is only a relatively narrow space between the dura and the brain.

Another type of conventional medical electrode is similar to the strip electrode in construction, but includes an array of electrical contacts. Thus, such an electrode generally includes two dielectric layers between which a plurality of flat electrical contacts are arranged in the form of a two-dimensional array with at least a portion of each contact exposed by an aperture in one of the dielectric layers.

BRIEF SUMMARY OF THE INVENTION

The invention is directed to an implantable medical electrode supporting at least one conductive contact having an edge portion and a rounded protrusion extending above the edge portion and adapted to contact a treatment site of a patient in use. The edge portion borders at least a portion of the rounded protrusion. The conductive contact overcomes drawbacks associated with contacts used in conventional medical electrodes by ensuring more reliable contact with the treatment site. The rounded protrusion of the contact causes friction between the contact and the treatment site, thereby facilitating precise positioning and maintenance of such positioning in use. Further, the friction created by the rounded protrusion permits a thinner overall electrode structure to be used since, conventionally, the thickness of the electrode structure was relied upon to prevent movement of the electrode. Thinner electrodes are desirable in order to avoid raising intracranial pressure when the dura is closed, particularly in pediatric cases, in which there is only a relatively narrow space between the dura and the brain.

The implantable medical electrode includes a first insulating layer and a second insulating layer having a plurality of apertures therethrough. A plurality of conductive contacts, each having an edge portion and a rounded protrusion as described, are positioned between the first and second insulating layers. In particular, each conductive contact is aligned with, and extends into a corresponding aperture of the second insulating layer. In one embodiment, the rounded protrusion extends through the respective aperture to terminate at an apex beyond the second insulating layer.

The conductive contacts may be arranged in the electrode in various patterns, including a single row of contacts or a two-dimensional array of contacts. Further, the number of conductive contacts provided in the electrode can be readily varied to suit a particular application.

The conductive contacts may take various shapes. As one example, the edge portion bordering the rounded protrusion is substantially flat. Alternatively, the edge portion may be rounded. The rounded protrusion of the conductive contact has a first rounded surface for contacting the treatment site in use and a second, opposing surface. In one embodiment, the second, opposing surface is rounded in a manner complementary to the first surface and, in an alternate embodiment, the second, opposing surface is substantially flat.

The height of the contact (from the base of the edge portion to the apex of the rounded protrusion) is selected as a function of the thickness of the second insulating layer. In particular, the contact height is greater than or substantially equal to the thickness of the second insulating layer in order to ensure that the apex of the rounded protrusion extends beyond the second insulating layer in use to contact the treatment site.

The conductive contacts may be comprised of various biocompatible materials, including platinum, stainless steel, gold, and conductive polymers. Similarly, each of the first and second insulating layers may be comprised of various biocompatible materials, such as polymers including silicone, polyamide, polyester, polytetrafluoroethylene, polyethylene, polypropylene, and hydrogels.

A plurality of conductors are provided, each one having a proximal end electrically connected to a corresponding one of the conductive contacts and a distal end electrically connected to a terminal adapted for connection to electrical stimulation and/or monitoring apparatus. Various techniques are suitable for electrically connecting the conductors to the contacts, such as soldering.

Also described is a method of forming a conductive contact with a rounded protrusion, including the steps of providing a substantially flat conductive element having first and second surfaces and placing the first surface of the contact over an anvil having a substantially round detent. Force is applied to the second surface of the substantially flat conductive element in order to force at least a portion of the conductive element into the substantially round detent to form the rounded protrusion. With this arrangement, the rounded protrusion has a first, rounded surface and a second, opposing surface which is rounded in a complementary manner with respect to the first surface.

Various other fabrication techniques are also possible, some of which provide the conductive contact with different shapes and features. As one example, a conductive contact is provided with the rounded protrusion having a first, rounded surface and a second, opposing surface which is substantially flat.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
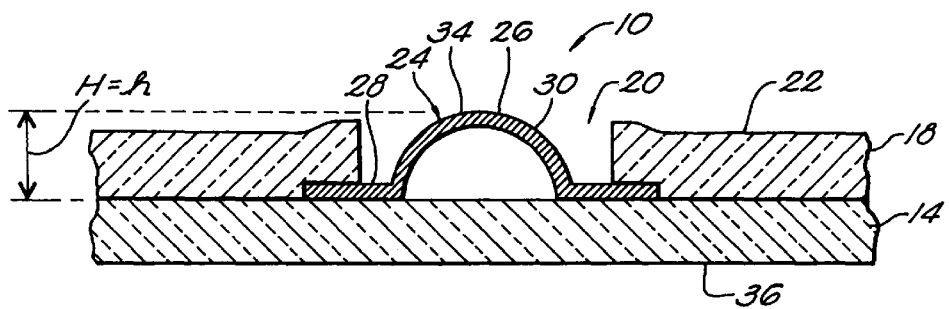
FIG. 1 is a cross-sectional view of a medical electrode including a conductive contact according to the invention.

Referring to FIG. 1, an implantable medical electrode 10 includes a first insulating layer 14 and a second insulating layer 18. The second insulating layer 18 has at least one aperture 20 therein. The electrode 10 further includes at least one conductive contact 24 having a rounded protrusion 26 and an edge portion 28 bordering at least a portion of the rounded protrusion. The conductive contact 24 is positioned between the first and second insulating layers 14, 18, respectively, such that the rounded protrusion 26 of the contact is aligned with the aperture 20. More particularly, the rounded protrusion 26 extends at least into the aperture and may, as shown, extend through the aperture to terminate at an apex 34 beyond the aperture 20 (i.e., beyond an exposed surface 22 of the second insulating layer 18).

Figure 5:
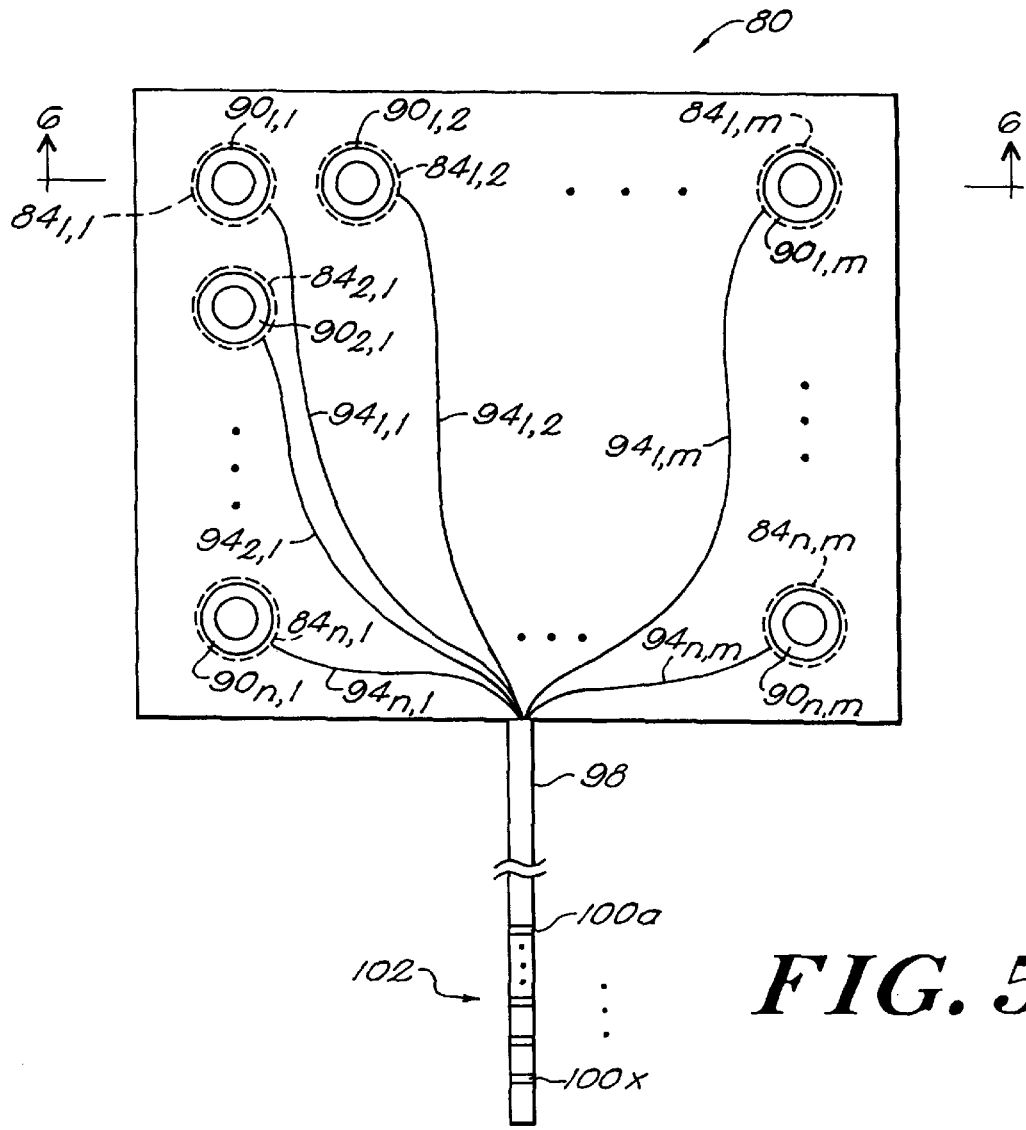
FIG. 5 is a plan view of a medical electrode array according to the invention.
Figure 6:
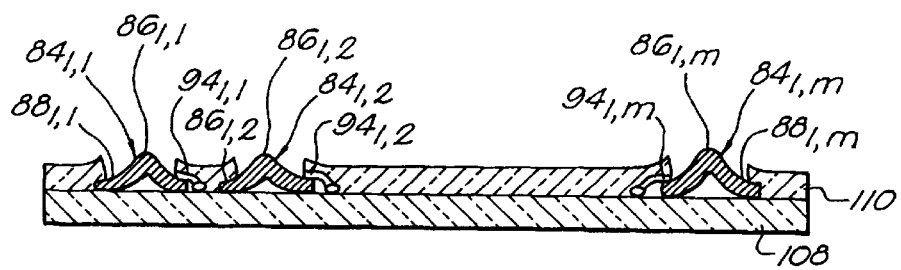
FIG. 6 is a cross-sectional view of the medical electrode array taken along line 6—6 of FIG. 5.

The electrode 10 generally includes a plurality of electrical contacts 24, each aligned with and extending into a corresponding aperture 20 in the second insulating layer 18. The contacts 24 may be arranged in various patterns to provide the electrode 10, such as a strip pattern containing a single row of contacts or an array containing a two-dimensional array of contacts (FIGS. 5 and 6).

Figure 2:
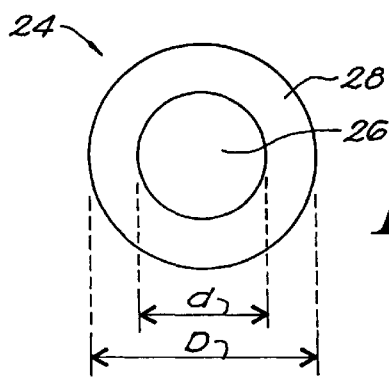
FIG. 2 is a plan view of the conductive contact of the medical electrode of FIG. 1.

Referring also to FIG. 2, the rounded protrusion 26 of the conductive contact 24 is bordered by the edge portion 28 which, in the illustrative embodiment, has a substantially round footprint. It will be appreciated by those of ordinary skill in the art that various other footprint shapes for the edge portion 28 are possible without departing from the spirit and scope of the invention. While the entire rounded protrusion 26 is bordered by the edge portion 28 in the embodiment of FIGS. 1 and 2, it is possible that only a portion of the protrusion 26 may be bordered by the edge portion 28.

The rounded protrusion 26 of the conductive contact 24 has a first, rounded surface 30 which contacts a treatment site of a patient in use. A second, opposing surface 32 of the rounded protrusion 26 is rounded in a manner complimentary to the first, rounded surface 30.

Various manufacturing techniques may be used to provide the conductive contact 24. As one example, the conductive contact 24 is fabricated from a substantially flat, disk-shaped conductive element having first surface 30 and second surface 32. The disk-shaped element is placed over an anvil having a substantially round detent, with the first surface 30 of the contact over the detent. Force is applied to the second surface 32 of the contact of a magnitude sufficient to deform a portion of the disk-shaped conductive element into the detent to provide the rounded protrusion 26.

It will be appreciated by those of ordinary skill in the art that various shapes are possible for the conductive contact 24 without departing from the spirit and scope of the invention. Two alternative shapes for the contact 24 are described below in conjunction with FIGS. 3 and 4.

Various conductive materials are suitable for providing the conductive contact 24. Preferably, the material of the contact is biocompatible. Examples of suitable materials include platinum, stainless steel, gold, and conductive polymers. Platinum is sometimes preferred due to its compatibility with magnetic resonance imaging (MRI) technology.

The dimensions of the conductive contact 24 may be readily varied to suit a particular application. In general, the contact 24 can be characterized as having a height "H" (FIG. 1) and a diameter "D" (FIG. 2). The rounded protrusion 26 of the contact has a height "h" (FIG. 1) which may be either less than the height "H" of the contact if the edge portion 28 is not flat or, alternatively, may be substantially equal to the height "H" of the contact if the edge portion is substantially flat.

In general, the height "H" of the contact 24 is substantially equal to or is slightly greater than the thickness of the second insulating layer 18, in order to ensure that the apex 34 of the rounded protrusion 26 contacts the treatment site of the patient in use. More particularly, in applications in which the second insulating layer 18 is comprised of a material that compresses in use, the contact height "H" may be greater than or substantially equal to the thickness of the second insulating layer 18 and in some cases may even be slightly less than the thickness of the second insulating layer 18. Compression of the second insulating layer 18 in use ensures that the apex 34 of the rounded protrusion 26 of the substantially rigid contact 24 contacts the treatment site in use. Alternatively, if the material of the second insulating layer 18 is not compressed in use, then the height "H" of the contact 24 is selected to be greater than the thickness of the layer 18 in order to ensure that the apex 34 of the rounded protrusion 26 extends through the aperture 20 and beyond the exposed surface 22 of the layer 18 to contact the treatment site. In the illustrative embodiment, each of the first and second insulating layers 14, 18 has a thickness on the order of 0.01 inches and the height "H" of the contact and the height "h" of the rounded protrusion 26 are on the order of 0.01 to 0.03 inches.

The rounded protrusion 26 further has a diameter "d" (FIG. 2) which may be equal to or less than the diameter "D" of the contact. More particularly, the diameter "d" of the rounded protrusion 26 is substantially equal to the contact diameter "D" in applications in which the edge portion 28 is a rounded "extension" of the rounded protrusion 26, as in the embodiment of FIG. 4. Alternatively, if the edge portion 28 is substantially flat, then the rounded protrusion diameter "d" is less than the contact diameter "D," as in the embodiment of FIG. 1. In the illustrative embodiment, the diameter "D" of the contact 24 is on the order of 0.200 inches and the diameter "d" of the rounded protrusion 26 is on the order of 0.125 inches.

In the illustrative embodiment, the thickness of the contact 24 is on the order of 0.002 inches. However, it will be appreciated by those of ordinary skill in the art that the contact thickness can be varied to suit a particular application and contact shape.

The aperture 20 through the second insulating layer 18 has a diameter which is less than the diameter "D" of the contact 24. In the illustrative embodiment, the aperture diameter is on the order of 0.125 inches. With these relative dimensions, in assembly, the second insulating layer 18 covers at least part of the edge portion 28 and serves to retain the contact 24 in place over the first insulating layer 14.

Various materials are suitable for providing the dielectric, or electrically insulating layers 14 and 18. Preferably, the material of the insulating layers is a known biocompatible material, such as polymers including silicone, polyamide, polyester, polytetrafluoroethylene, polyethylene, polypropylene, and hydrogels. The thickness of the insulating layers 14, 18 may be the same or different from each other and may be readily varied to suit a particular application. In the illustrative embodiment, each of the insulating layers 14, 18 has a thickness on the order of 0.01 inches.

Various techniques can be used to assemble the electrode 10 of FIG. 1. As one example, the second insulating layer 18 is positioned with the surface 22 facing down on a work surface. The conductive contact 24 is then inserted into the aperture 20 of the insulating layer 18 with the rounded protrusion 26 centered within and extending into the aperture 20. The rounded protrusion 26 thus provides an additional advantage of simplifying manufacture by providing a registration feature. That is, proper placement of the contact 24 relative to the aperture 20 is facilitated by positioning the rounded protrusion 26 within the aperture. With the contact 24 thus positioned, the first insulating layer 14 is positioned over the second insulating layer 18. An adhesive may be used to secure the first insulating layer 14 to the second insulating layer 18, thereby causing the contact 24 to be retained within the aperture 20, with the edge portion 28 in contact with a portion of the second insulating layer 18 surrounding the aperture 20 which holds the contact in place. Other suitable techniques for securing the insulating layers together include ultrasonic bonding and the use of partially cured silicone.

In use, the electrode 10 is positioned over a treatment site of a patient, such as the cortex, with the apex 34 of the contact 24 in physical and electrical contact with the treatment site. The dura is brought over the exposed surface 36 of the insulating layer 14 and sutured back in place. With this arrangement, pressure is exerted on the electrode 10 so as to urge the contact 24 against the cortex.

Friction between the rounded protrusion 26 and the treatment site serves to maintain the contact 24 and the entire electrode 10 in its precise location. It will be appreciated by those of ordinary skill in the art that the friction between the apex 34 of the rounded protrusion 26 and the treatment site which serves to maintain the contact 24 and electrode 10 in position also permits the use of thinner insulating layers 14, 18 than otherwise possible. This is because, conventionally, the overall thickness of the electrode 10 was relied upon to hold the electrode in place and, thus, could not be decreased beyond a predetermined thickness without risking slippage of the electrode once implanted.

Figure 3:
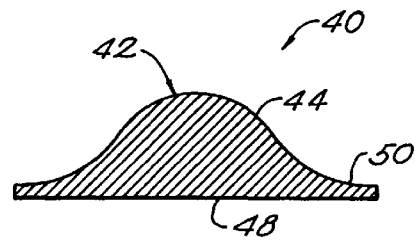
FIG. 3 is a cross-sectional view of an alternate conductive contact according to the invention.

Referring to FIG. 3, an alternative conductive contact 40 for use with an electrode assembly of the type shown in FIG. 1 has a rounded protrusion 42, an edge portion 50, a first surface 44, and a second, opposing surface 48. The first surface 44 of the contact 40 is rounded, similar to the surface 30 of contact 24 (FIG. 1). However, the second surface 48 of contact 40 is substantially flat, as contrasted to the rounded surface 32 of contact 24 (FIG. 1).

In assembly, the conductive contact 40 is positioned between first and second insulating layers 14, 18, respectively, in the manner described above in conjunction with the electrode 10 of FIG. 1. Thus, in assembly, the edge portion 50 of the contact 40 is covered by a portion of the second insulating layer 18 surrounding the aperture 20 which serves to hold the contact 40 in place.

Figure 4:
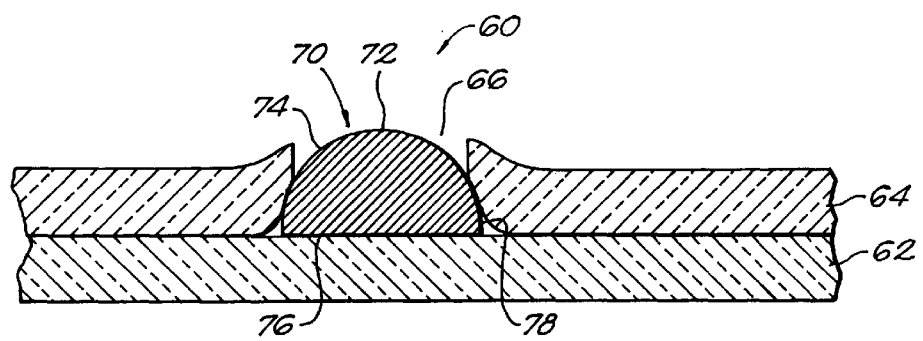
FIG. 4 is a cross-sectional view of a medical electrode according to an alternate embodiment of the invention.

Referring to FIG. 4, an alternative electrode 60 includes first and second insulating layers 62, 64, respectively, which are substantially identical to insulating layers 14, 18, respectively, of the electrode 10 of FIG. 1. A conductive contact 70 is disposed within an aperture 66 of the second insulating layer 64, as shown. The conductive contact 70 has a rounded protrusion 72 and an edge portion 78. The rounded protrusion 72 has a first, rounded surface 74 and a second, opposing surface 76 which is substantially flat.

The contact 70 differs in shape from the contacts 24 and 40 of FIGS. 1 and 3, respectively. In particular, the contact 70 has a substantially hemispherical shape. Thus, the edge portion 78 is rounded and, in fact, is a substantially continuous "extension" of the rounded protrusion 72. Thus, the diameter "d" of the rounded protrusion 72 is substantially equal to the diameter "D" of the contact 70.

In assembly, the contact 70 is positioned between the first and second insulating layers 62, 64, respectively, in the manner described above in conjunction with the electrode 10 of FIG. 1. In particular, the contact is positioned within the corresponding aperture 66 of the second insulating layer 64 such that the edge portion 78 of the contact is covered by a portion of the second insulating layer 64 surrounding the aperture 66. Securing the first insulating layer 62 and the second insulating layer 64 together, such as with an adhesive, causes the contact 70 to be held in place.

Referring to FIG. 5, an alternative electrode 80 supports a plurality of conductive contacts $84_{1,1}$–$84_{n,m}$ arranged in a two-dimensional, n×m array. Each such contact $84_{1,1}$–$84_{n,m}$ has a rounded protrusion $86_{1,1}$–$86_{n,m}$ (shown in FIG. 6 for contacts $84_{1,1}$–$84_{1,m}$) bordered, at least in part, by an edge portion $88_{1,1}$–$88_{n,m}$ (shown in FIG. 6 for contacts $84_{1,1}$–$84_{1,m}$), respectively.

A plurality of conductors $94_{1,1}$–$94_{n,m}$ are provided for coupling to respective conductive contacts $84_{1,1}$–$84_{n,m}$, as shown. More particularly, each of the conductors has a proximal end electrically connected to the respective contact and extends from the respective contact to terminate at a distal end. In the illustrative embodiment, the distal ends of the plurality of conductors $94_{1,1}$–$94_{n,m}$ are collectively insulated by an insulator 98 which terminates at an end 102 with a plurality of conductive rings 100a–100x, as shown. Each of the conductive rings 100a–100x is electrically connected to a respective one of the conductors $94_{1,1}$–$94_{n,m}$. The insulator end 102 is similar in form to a depth electrode in the use of ring electrodes and may use similar techniques to permit electrical connections to be made to the plurality of contacts $84_{1,1}$–$84_{n,m}$.

Referring also to FIG. 6, a cross-sectional view of the electrode array 80 of FIG. 5 illustrates that the electrode 80 includes a first insulating layer 108 and a second insulating layer 110 having a plurality of apertures therethrough. Each of the conductive contacts $84_{1,1}$–$84_{n,m}$ is aligned with and extends at least into a respective aperture $90_{1,1}$–$90_{n,m}$ of the electrode array 80, as shown for contacts $84_{1,1}$–$84_{1,m}$.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A medical electrode comprising:

a first insulating layer;

a second insulating layer having at least one aperture therethrough; and at least one dome-shaped conductive contact aligned with the aperture and having a rounded protrusion extending into the at least one aperture and an edge portion disposed between the first and second insulating layers, the at least one contact being adapted for contacting a surface of a patient's brain such that friction between the rounded protrusion and the brain is effective to substantially maintain the position of the medical electrode on the brain surface.

2. The electrode of claim 1 wherein the edge portion borders at least a portion of said rounded protrusion and is disposed in contact with said second insulating layer.

3. The electrode of claim 1 wherein the rounded protrusion of said at least one conductive contact extends through said at least one aperture to terminate beyond said second insulating layer.

4. The electrode of claim 1 wherein said at least one conductive contact is comprised of a material selected from the group consisting of platinum, stainless steel, gold, and conductive elastomer.

5. The electrode of claim 1 wherein each of said first and second insulating layers is comprised of a polymer.

6. The electrode of claim 1 further comprising a selected one of an adhesive and partially cured silicone disposed between said first and second insulating layers.

7. The electrode of claim 1 wherein the rounded protrusion of said at least one conductive contact has a diameter and a height and wherein the height of the rounded protrusion is less than or equal to the diameter of the rounded protrusion.

8. The electrode of claim 1 wherein said at least one conductive contact has a height and said second insulating layer has a thickness and wherein said height of said at least one conductive contact is greater than or substantially equal to said thickness of said second insulating layer.

9. The electrode of claim 1 further comprising at least one conductor electrically connected to said at least one conductive contact.

10. The electrode of claim 9 further comprising at least one terminal electrically connected to said at least one conductor for permitting electrical contact to be made to said at least one conductive contact.

11. A method of manufacturing a medical electrode, comprising the steps of:

providing a first insulating layer;

providing a second insulating layer having at least one aperture therethrough;

providing at least one dome-shaped conductive contact having an edge portion and a rounded protrusion; and positioning the at least one conductive contact between said first and second insulating layers so that the rounded protrusion of said at least one conductive contact is aligned with and extends into said at least one aperture of said second insulating layer, wherein said edge portion of said at least one conductive contact is disposed in contact with said second insulating layer adjacent to the at least one aperture of said second insulating layer, wherein the at least one contact is adapted for contacting a surface of a patient's brain such that friction between the rounded protrusion and the brain is effective to substantially maintain the position of the medical electrode on the brain surface.

12. The method of claim 11 wherein the rounded protrusion of said at least one conductive contact has an apex and wherein said positioning step comprises the step of positioning said at least one conductive contact between the first and second insulating layers so that the apex of the rounded protrusion of said at least one conductive contact extends beyond the second insulating layer.

13. The method of claim 11 wherein the rounded protrusion of said at least one conductive contact has a diameter and a height and wherein the step of providing at least one conductive contact comprises the step of providing the rounded protrusion with a height equal to or less than the diameter of the rounded protrusion.

14. The method of claim 11 wherein said at least one conductive contact has a height and said second insulating layer has a thickness and wherein the step of providing the at least one conductive contact comprises the step of providing said conductive contact with a height greater than or substantially equal to the thickness of said second insulating layer.

15. The method of claim 11 wherein the step of providing at least one conductive contact comprises the steps of:

providing a substantially flat conductive element having a first surface and a second surface;

placing the first surface of said substantially flat conductive element over an anvil having a substantially round detent; and applying a force to the second surface of said substantially flat conductive element in order to force a portion of said conductive element into said substantially round detent to form said rounded protrusion.

16. The method of claim 11 wherein the step of providing at least one conductive contact comprises the step of providing the edge portion to be substantially flat.

17. The method of claim 11 wherein the step of providing at least one conductive contact comprises the step of providing the edge portion to be rounded.

* * * * *